United States Patent [19]

Woodriff

[11] Plant 4,212

[45] Feb. 7, 1978

[54] BEGONIA PLANT

[75] Inventor: Leslie Woodriff, McKinleyville, Calif.

[73] Assignee: Mikkelsens, Inc., Ashtabula, Ohio

[21] Appl. No.: 773,317

[22] Filed: Mar. 1, 1977

[51] Int. Cl.[2] ..... A01H 5/00

[52] U.S. Cl. ..... Plt./68

[58] Field of Search ..... Plt./68

*Primary Examiner*—Robert E. Bagwill
*Attorney, Agent, or Firm*—Donald D. Jeffery

[57] ABSTRACT

A begonia cultivar being similar to Tiger Kitten, but having shorter petioles and a spiraled leaf base.

1 Drawing Figure

The present invention relates to a new and distinctive cultivar of begonia plant, botanically known as *Begonia rhizomatous* and known by the cultivar name Leprechaun.

The new cultivar was discovered by me as a seedling from a controlled crossing of Botique (not patented) as the seed parent with Tiger Kitten, as the pollen parent. Tiger Kitten is disclosed in my U.S. Plant Pat. No. 3,968, granted Oct. 26, 1976. Asexual reproduction of the new cultivar by leaf cuttings has reproduced the unique features of the new cultivar through successive propagations.

The following combination of characteristics distinguish the new begonia from both its parent and other begonias commercially known and used in the floriculture industry:

1. There is a general resemblance to the cultivar Tiger Kitten as to the leaf coloration and color patterns.
2. Leprechaun has spirals at the leaf base, whereas Tiger Kitten does not. The leaf apex of Leprechaun is sharply acute.
3. The leaf petiole is very short whereas the petiole of Tiger Kitten is long, allowing it to cascade over the sides of a container.
4. Leprechaun is very short in growth, being most useful as a rounded, compact, short upright plant especially useful in small pots up to 10–12 cm. in diameter.
5. The overall propagation time is slower for Leprechaun than for Tiger Kitten; the same is true for the growth rate.
6. Leprechaun is a very hardy durable begonia plant that can tolerate up to 7–10 days without watering in the normal home environment.
7. The coloration is quite distinctive with clear brown areas surrounding the veins and bright green areas between the veins.
8. Flowering is insignificant for general commercial consideration, being sparse and infrequent during the winter months. In comparison, flowering of both Tiger Kitten and the cultivar Roulette is quite profuse during the winter months, making those cultivars more valuable than first considered. The cultivar Roulette is disclosed in my pending application for U.S. Plant Pat. Ser. No. 691,484, filed June 1, 1976.

The accompanying colored photograph illustrates the new cultivar and shows the colors as true as it is reasonably possible to obtain in a colored reproduction of this type.

The following is a detailed description of my new begonia cultivar based on plants produced under commercial practices in greenhouses at McKinleyville, Calif. and Ashtabula, Ohio. Color references are made to the Royal Horticultural Society Colour Chart except where general color terms of ordinary dictionary significance are used.

Parentage: Botique crossed with Tiger Kitten.

Propagation: By leaf cuttings that root in 24–28 days at 22° C. Basal adventitious buds then initiate and emerge above the media in 45 to 60 additional days.

Rooting habit: Rooting and shooting is nearly 100% on all leaves propagated regardless of where the location the leaves were on the stock plant. Although rooting is somewhat slower than for the cultivar Tiger Kitten, the quantity eventually is as good, dendritic, fibrous and hardy.

Habit of growth: Slow, extremely compact, short petioles, top of plant rounded, height is less than diameter.

Blooming season: Normally in winter months from December to April or May.

Blooming habits: Compound cymes on stems arising from the rhizome as do the leaves.

Foliage: Extremely abundant, arising at very close nodes on the rhizomes, with the rhizomes dividing themselves rapidly.

- *Size.*—In 12 cm. pots leaves are uniformly 5–6 cm. in diameter, with oldest lower leaves 7 cm. wide by 10 cm. long.
- *Shape.*—Ovate, unsymmetrical, apex acute, basal lobes spiraled.
- *Texture.*—Firm, crisp, smooth, iridescent.
- *Margin.*—Dentate, ciliate.
- *Color.*—Bi-color, veinal zone, near greyed orange 166A fading to greyed orange 165A with green infusion; interveinal zone generally darker than yellow green 145A.

Disease resistance: No diseases noted to date.

Flowers:

- *Borne.*—Individually on small pedicels 7–10 mm. long by 1 mm. in diameter supported from the peduncle arising from the rhizome. Total height of flowering cymes upwards to 15 cm. above the top of the leaf canopy. Both pedicels and peduncles are speckled with blotches of red and are pubescent.
- *Quantity.*—Flower quantity considered sparse.
- *Buds.*—Approximately 10 mm. before opening.
- *Tepals.*—Two in number, each 10 mm. in diameter, light pink to white, red flecking on underside.

*Reproductive organs.*—Stamens: Greenish yellow to yellow. Pollen: Light yellow. Styles/Ovaries: Three yellow stigmas on yellow styles and three ovaries, light pink and approximately 5 mm. long.

I claim:

1. A new and distinct cultivar of begonia plant known by the cultivar name Leprechaun and particularly characterized as to uniqueness by the combined characteristics of leaf coloration and color pattern, with the leaves having clear brown areas surrounding the veins and bright green areas between the veins; leaves having spirals at the base and short petioles; short growth habit and relatively slow propagation time and growth rate; superior hardiness, and generally insignificant flowering from a commercial standpoint.

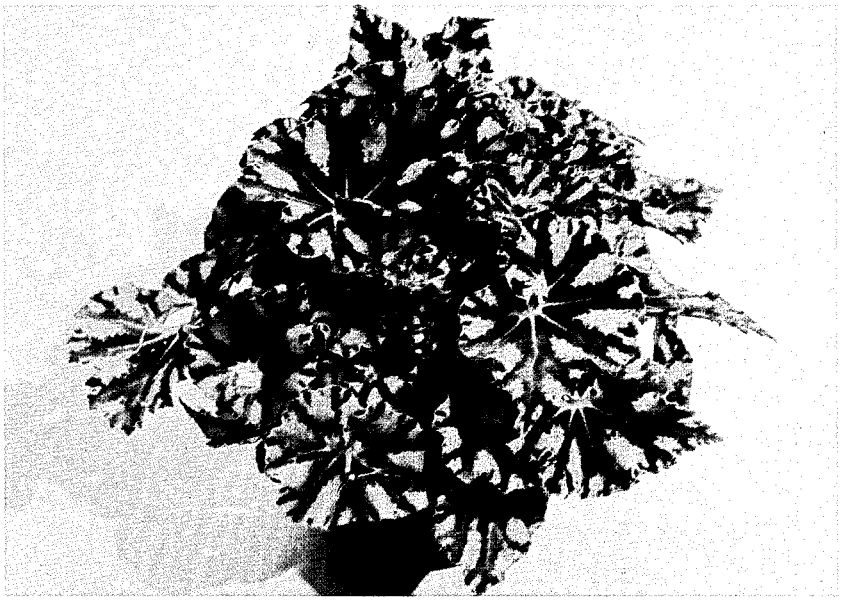

* * * * *